United States Patent [19]

Harrison

[11] 4,064,070

[45] Dec. 20, 1977

[54] CATALYST FOR PRODUCING MALEIC ANHYDRIDE

[75] Inventor: Jonas P. Harrison, Pinole, Calif.

[73] Assignee: Chevron Research Company, San Francisco, Calif.

[21] Appl. No.: 729,335

[22] Filed: Oct. 4, 1976

Related U.S. Application Data

[62] Division of Ser. No. 535,456, Dec. 23, 1974, abandoned.

[51] Int. Cl.$^2$ .............................................. B01J 27/14
[52] U.S. Cl. .................................... 252/435; 252/437; 260/346.75
[58] Field of Search ............................... 252/435, 437

[56] References Cited

U.S. PATENT DOCUMENTS

| | | | |
|---|---|---|---|
| B 330,354 | 1/1975 | Mount et al. | 252/435 X |
| 2,054,865 | 9/1936 | Oxley et al. | 252/435 X |
| 2,738,336 | 3/1956 | Mavity | 252/435 |
| 3,156,706 | 11/1964 | Kerr | 252/437 X |
| 3,183,196 | 5/1965 | Watanabe et al. | 252/456 |
| 3,293,268 | 12/1966 | Bergman et al. | 252/437 X |
| 3,888,886 | 6/1975 | Young et al. | 252/435 X |
| 3,915,892 | 10/1975 | Harrison | 252/435 |
| 3,985,775 | 10/1976 | Harrison | 252/437 X |
| 3,987,063 | 10/1976 | Lemal et al. | 252/437 X |

*Primary Examiner*—Patrick P. Garvin
*Assistant Examiner*—William G. Wright
*Attorney, Agent, or Firm*—D. A. Newell; John Stoner, Jr.; W. Keith Turner

[57] ABSTRACT

A process for producing maleic anhydride which comprises partially oxidizing a hydrocarbon feed at a temperature in the range 300°–600° C by contacting said feed and an oxygen-containing gas with a catalyst comprising vanadium, phosphorus and silicon oxides prepared by steps comprising coprecipitating vanadium oxide and silica or a silica precursor. Preferably an organic silicon compound, especially an alkyl orthosilicate, is used to form the silica precipitate. Preferably the organic silicon compound is added so as to coprecipitate both during the reduction of the vanadium from a +5 oxidation state to a 3.5–4.6 oxidation state and also is added or is present so as to precipitate silica or a silica precursor simultaneously with the reaction of phosphoric acid with the reduced vanadium.

5 Claims, No Drawings

CATALYST FOR PRODUCING MALEIC ANHYDRIDE

This is a division of application Ser. No. 535,456, filed Dec. 23, 1974 now abandoned.

BACKGROUND OF THE INVENTION

The present invention relates to hydrocarbon oxidation catalysts and catalyst preparation and especially to a hydrocarbon oxidation process for producing maleic anhydride using a catalyst prepared in a certain manner and containing vanadium, phosphorus and silicon oxides.

The use of catalysts containing vanadium, phosphorus and silicon oxides for oxidation of hydrocarbons to maleic anhydride is disclosed in a general fashion in many prior art references. For example, U.S. Pat. No. 2,778,838 to Reid et al discloses the use of various supports such as kieselguhr (mostly silica) for a vanadium-phosphorus oxide catalyst used in the production of maleic anhydride. According to the Reid et al patent, the support is an inert carrier for the vanadium and phosphorus oxides.

U.S. Pat. Nos. 3,156,705, 3,156,706, 3,156,707, 3,238,254, 3,255,211, 3,255,212, 3,255,213, 3,288,721, 3,351,565, and 3,385,796 to Kerr also disclose in a general fashion the use of various materials, including silica, as a support for a vanadium-phosphorus oxide catalyst used in producing maleic anhydride, in particular from an unsaturated hydrocarbon feed such as butene. These patents to Kerr usually mention the use of silica materials as a support and/or as inert diluents and not as part of the catalyst material coprecipitated with vanadium and phosphorus oxides. Apparently all the patents to Kerr state (see, for example, Col. 5, lines 32-39 of U.S. Pat. No. 3,156,707) substantially as follows:

"Inert diluents such as silica may be present in the catalyst, but the combined weight of the essential ingredients phosphorus, oxygen and vanadium should preferably consist essentially of at least about 50 weight percent of the composition which is coated on the carrier, if any, and preferably these components are at least about 75 percent of the composition coated on the carrier, and more preferably at least 95 weight percent."

U.S. Pat. No. 3,226,337 to Riemenschneider et al also mentions the use of silica as an inert carrier at Col. 1, line 46, and Col. 2, line 43. U.S. Pat. No. 3,293,268 to Bergman et al mentions the use of silicon carbide as an inert carrier at Col. 3, line 60. Also, U.S. Pat. No. 3,759,848 to Felice mentions the use of silica as an inert support.

Patents outside the maleic anhydride production area but of interest regarding the disclosure of the use of silica in catalysts include U.S. Pat. Nos. 1,463,206, 1,852,207 and 2,086,542, all of which are early patents relating to the use of vanadium oxide on a support, for example a siliceous support, as an oxidation catalyst.

U.S. Pat. Nos. 2,120,702, 2,275,182, 2,575,457, 2,613,187, 2,694,686, 3,132,109, 3,213,035 and 3,673,111 disclose the use of phosphoric acid on a support, such as a silica support, as olefin polymerization catalysts. The catalysts are typically produced by impregnating phosphoric acid onto a porous support and calcining, but the catalysts can be produced by alternate methods. For example, in U.S. Pat. No. 2,613,187, a catalyst is prepared by mixing pyrophosphoric acid, diatomaceous earth, and a polymeric dimethyl siloxane to form a composite, and calcining said composite.

U.S. Pat. Nos. 3,243,385 and 3,480,564 relate to vanadium-containing ammoxidation catalysts useful for oxidation of olefins to acrylonitrile. The catalyst of U.S. Pat. No. 3,243,385, for example, can be prepared using ammonium metavanadate, phosphoric acid, colloidal silicic acid and tin nitrate.

U.S. Pat. No. 3,351,566 discloses stabilization of a nickel surface area of a nickel-silica catalyst wherein the catalyst is prepared by coprecipitating a nickel cation with a silicate anion onto a porous solid silica.

U.S. Pat. Nos. 3,183,196 and 2,738,336 are of special interest with respect to the present invention. U.S. Pat. No. 3,183,196 discloses a catalyst for oxidation of hydrocarbons such as oxidizing orthoxylene to phthalic anhydride, benzene to maleic anhydride, and anthracene to anthraquinone. The catalyst of the '196 patent is prepared by producing a hydrate of silica (for example, by kneading the silica in water), adding a vanadium compound to said hydrate to obtain a pasty mixture, and adding any other components desired and then calcining.

U.S. Pat. No. 2,738,336 is particularly directed to preparing an olefin polymerization catalyst somewhat similar to the olefin polymerization catalysts of the patents previously cited. However, instead of the typical impregnation of phosphoric acid onto a support, according to the '336 patent disclosure the catalyst is made by mixing a polyphosphoric acid and an alkyl orthosilicate and then calcining the composite. According to the date discussed in the patent at Col. 5, using the alkyl orthosilicate results in a better silica-containing catalyst for propylene polymerization than when the catalyst is made using kieselguhr.

SUMMARY OF THE INVENTION

According to the present invention, a process is provided for producing maleic anhydride which process comprises partially oxidizing a hydrocarbon feed at a temperature in the range 300°-600° C by contacting said feed and an oxygen-containing gas with a catalyst comprising vanadium, phosphorus and silicon oxides prepared by steps comprising coprecipitating vanadium oxide and silica or a silica precursor.

Among other fators, the present invention is based on my finding that a catalyst with unexpectedly high selectivity and also surprisingly good yield stability after exposure to high temperature is obtained by precipitating silica with vanadium and phosphorus oxides.

Preferably the material used to form the silica precipitate with the vanadium and phosphorus oxides is an organic silicon compound, preferably an organic silicate or alkoxide, especially alkyl orthosilicates.

Other organosilicon compounds containing reactive silicon bonded to both carbon and inorganic elements which can be used include: hydrocarbyl oxysilanes, e.g., $CH_3Si(OC_2H_5)_3$; silazanes, e.g., $(CH_3)_2SiHN-HSiH(CH_3)_2$, wherein the reactive bond is —NH—; and generally hydrocarboxysilicates or organosilicon esters.

The alkyl silicate-type procedure for preparing the catalyst is especially advantageous in an organic medium preparation of the catalyst as opposed to an aqueous medium preparation of the catalyst.

Organic medium preparations are exemplified, for instance, by commonly assigned applications Ser. Nos. 298,074 and 359,294, the disclosures of which applications are incorporated by reference herein, particularly in that they relate to vanadium-phosphorus oxide catalyst preparations useful in the present invention if coupled with the silica precipitation aspect of the present invention.

Aqueous-type preparations are illustrated, for instance, by the Kerr patents and also the Bergman patent referred to above under "Background of the Invention." When using an alkyl silicate in accordance with a preferred procedure of the present invention, water, produced, for example, in the reduction of vanadium pentoxide to a lower vanadium oxidation state, can be advantageously removed by the following reaction:

$$(RO)_4Si + 2H_2O \rightarrow 4ROH + SiO_2$$

I have found it is particularly preferably to use the alkyl silicate preparation procedure to control water content of the catalyst mix during catalyst preparation to produce a vanadium-phosphorus-silicon oxide catalyst which contains only a small amount of water of hydration, for example about 1–3 mols water of hydration per mol of the catalyst formulation. This water of hydration is that which is left after only moderate drying at temperatures below about 150° C as opposed to higher calcination temperatures.

Typically, in forming the catalyst of the present invention, vanadium pentoxide is used as a starting material and during its reduction water is formed. According to a preferred procedure of the present invention, alkyl silicate is present during vanadium pentoxide reduction and will react with water formed during reduction of the vanadium pentoxide.

Also in the preferred procedure of the present invention, alkyl silicate is present during phosphoric acid combination with the vanadium oxide constituent of the catalyst. Thus, preferably the organic silicon compounds such as the alkyl silicate is added to the slurry mixture containing the reduced vanadium oxide so that the alkyl silicate will be present during the combination of the phosphoric acid with the vanadium constituent of the catalyst and so that the silica or silica precursor will precipitate simultaneously with the phosphorus oxide or phosphorus oxide precursor in addition to the silica which is precipitated simultaneously with the reduction of the vanadium pentoxide.

Thus, according to a preferred embodiment of the present invention, a process for producing maleic anhydride is provided wherein the catalyst used in the process is prepared by steps comprising: (a) reducing vanadium pentoxide to obtain vanadium of a lower oxidation state; (b) coprecipiating the silica or silica precursor with the reduced vanadium; and (c) reacting phosphoric acid with the reduced vanadium.

Preferably the vanadium oxide reduction is carried out using an alcohol effective to reduce the vanadium to an oxidation state between about 3.5 and 4.6.

As indicated above, preferably when the phosphoric acid is reacted with vanadium there is simultaneous precipitation of silica or the silica precursor.

If silica is not directly precipitated from the silicon compound used to form the catalyst or catalyst precursor material, the silicon compund used must be one which will form silica on calcination of the catalyst or catalyst material.

Preferably an alkyl silicate is used in the preparation procedure to obtain the silica component of the catalyst. Preferred alkyl silicates are those wherein the alkyl groups have 1 to 10 carbon atoms, for example tetaethylorthosilicate.

Although it is preferred in the present invention to use an organic silicon compound, particularly an organic silicate ester, according to an alternate mode inorganic silica compounds can be used, such as silicon halides, silicon oxyhalides, polysilanes, and halosilanes.

Hydrocarbon feeds for the process of the present invention can be hydrocarbons having 4–10 carbon atoms, for example aromatic hydrocarbons such as benzene, and, less desirably, orthoxylene and naphthalene. Saturated or mono- or diolefinic acyclic or cyclic hydrocarbons which have a carbon atom content in the range 4–10 and a linear chain of at least 4 carbon atoms can be used as feedstocks for the present invention. Especially preferred as a feedstock is normal butane.

As the oxygen-containing gas for the oxidation reaction over the catalyst, preferably air is used although purified oxygen can also be used.

Preferred pressures for the present invention are between atmospheric and 1000 psig, more preferably between 10 and 100 psig. Preferred space velocities are between 100 and 5000 volume gas/volume catalyst/hour, more preferably between 500 and 3000.

Preferred amounts of oxides of vanadium, phosphorus and silicon for the catalyst are atomic ratios of P:V=0.9-3:1 and P:Si=20-1:1, preferably P:V=1-1.3:1 and P:Si=16-10:1.

According to an alternate embodiment of the present invention, there is provided a novel catalyst especially useful for hydrocarbon oxidation such as hydrocarbon oxidation to maleic anhydride. The catalyst includes the catalysts described above and exemplified hereinbelow. Thus, the catalyst is prepared by steps comprising coprecipitating vanadium oxide and silica or a silica precursor.

The vanadium oxide can be precipitated as a hydrate or in another form of the vanadium which will form vanadium oxide upon calcination.

The silicon compound used in forming the catalyst may precipitate as silica or in another form, but in any case the silicon compound used upon calcination must yield silica.

EXAMPLES

Example 1 — Catalyst with no coprecipitated silica

A 500-ml, 3-necked flask, equipped with a mechanical stirrer, a thermometer, condenser with a Dean-Stark water trap, and an addition flask was charged with 50 g (0.275 mol) of vanadium pentoxide, 494 ml of isobutyl alcohol and 65 ml of benzyl alcohol. The contents were stirred and heated at reflux for 3 hours, during which time 2 ml of water was collected in the trap. Then 67 g (0.58 mol) of 85% phosphoric acid was added slowly while maintaining reflux. The resulting mixture was refluxed for an additional 3 hours, during which time 21 ml of water was removed.

After cooling the slurry to ambient temperature, the solid was removed by filtration, dried to about 20% (by weight) of solvent and tabletted into ⅛ inch-diameter pellets. These pellets were dried by heating at 150° C for 2 hours. They were then activated in a muffle furnace by first heating in air at 398° C for 2 hours. Then the temperature was slowly raised to 500° C over a period of one hour, during which time a mixture of nitrogen wth air (to give 13 % oxygen) was passed over the catalyst. Heating was continued at 500° C for 15 hours in the presence of this mixture.

Example 2 — Silica-modified catalyst preparation

The procedure of Example 1 was repeated, except that 15.6 g (0.075 mol) of tetraethylorthosilicate was added to the charge, and an additional 44.5 g (0.214 mol) was added just prior to charging the phosphoric acid. No water was removed or observed in the trap during this preparation. A product slurry coprecipitate was obtained. The slurry precipitate was worked up and activated as before.

The catalyst was submitted to an electron probe microanalysis which showed it to have 1.45 weight percent silica distributed uniformly throughout the pellet.

Example 3 — Silica-modified catalyst preparation

The procedure of Example 2 was followed, except that the additional quantity of tetraethylorthosilicate added prior to the phosphoric acid was only 22.8 g (0.11 mol). The final catalyst had 0.7 weight percent silica.

Example 4 — Silica-modified catalyst preparation

The procedure of Example 2 was followed except that all of the tetraethylorthosilicate, 86 g (0.414 mol) was added at one time, just prior to the addition of phosphoric acid. Analysis indicated 5.3 weight percent silica in the catalyst.

Example 5 — Silica-modified catalyst preparation

The procedure of Example 2 was repeated, except that 77.6 g (0.674 mol) of 85 weight percent phosphoric acid was used instead of 66 g.

Example 6

The above-prepared catalysts were tested in the oxidation of butane to produce maleic anhydride (MA) by an accelerated aging test. In this test method, 5 ml of the catalyst pellets are charged to a ½inch-diameter stainless-steel tubular reactor heated by a salt bath. Then a 1.5% butane-in-air mixture is passed over this catalyst charge at 2000 V/V/hr and atmospheric pressure. After steady-state reaction is reached (about 100 hours), the temperature is adjusted to give 60% conversion of butane. The yield of maleic anhydride at these conditions is determined. Then the catalyst is subjected to 20 hours of operation at 6000 V/V/hr with a hot-spot temperature of 500° C. At the end of this time, reaction conditions are returned to the previous values, and the yield of maleic anhydride determined. A comparison of yield before and after the accelerated aging test is an indication of catalyst stability. Results of applying this test to the catalysts prepared in the above examples is given in Table I.

TABLE I

Effect of Accelerated Aging on V-P-Si Catalysts

| Catalyst of Example | Selectivity[1] at 60% Conversion | | Activity[2] at 800° F | |
|---|---|---|---|---|
| | Before | After | Before | After |
| 1-no coprecip. Si | 98 | 91 | 2200 | 2200 |
| 2-1.45% Si | 115 | 108 | 5000 | 5300 |
| 3-5.3% Si | 106 | 102 | 3500 | 5400 |
| 4-0.7% Si | 111 | 114 | 4000 | 4600 |

[1]Selectivity = Yield of Maleic Anhydride based on Butane Converted =

TABLE I-continued

Effect of Accelerated Aging on V-P-Si Catalysts

| Catalyst of Example | Selectivity[1] at 60% Conversion | | Activity[2] at 800° F | |
|---|---|---|---|---|
| | Before | After | Before | After |

$$\frac{\text{grams of MA in product} \times 100}{\text{grams of butane fed} - \text{grams of butane recovered}}$$

[2]Activity (K) = Relative first order rate constant at 800° F = $\left( \frac{T \div 535}{P \div 14.7} \times \text{VHSV} \times \text{Ln}\frac{1}{1-x} \right) e^A$ wherein T = Average bed temperature (° R)
P = Average bed pressure (atm.)
VHSV = Volume of feed gas at 75° F & 1 atm. per volume of reactor bed per hour
x = mol fraction of n-butane converted
A = 16.54 (1260 - T/T)

The above-tabulated results show that the silica-containing catalysts prepared by the method of this invention have better initial activity and selectivity than a catalyst prepared in the same way without silica. Furthermore, the data indicate that the catalysts of this invention will improve in activity with use, whereas the prior art catalyst is generally unchanged. In one case, at low silica concentrations, the selectivity is also improved with use.

1. A catalyst comprising oxides of vanadium, phosphorus, and silicon prepared by steps comprising:
   a. coprecipitating vanadium oxide and an alkyl orthosilicate in an organic medium to form a coprecipitate of vanadium oxide and silica or a silica precursor and wherein the alkyl groups of the alkyl orthosilicate have 1 to 10 carbon atoms;
   b. coprecipitating phosphorus either simultaneously with the vanadium oxide and alkyl orthosilicate coprecipitation or thereafter to thereby obtain the catalyst precursor; and
   c. calcining the catalyst precursor to thereby obtain the silica-containing catalyst.

2. A catalyst in accordance with claim 1 wherein the vanadium pentoxide reduction is carried out using an alcohol effective to reduce the vanadium to an oxidation state between about 3.5 and 4.6.

3. A catalyst in accordance with claim 1 wherein the catalyst is prepared by steps comprising:
   a. reducing vanadium pentoxide to obtain vanadium of a lower oxidation state wherein said reducing is carried out either simultaneously with or prior to the coprecipitation of the silica or silica precursor with the vanadium oxide;
   b. coprecipitating at least a portion of the silica or silica precursor with the reduced vanadium; and
   c. reacting phosphoric acid with the reduced vanadium.

4. A catalyst in accordance with claim 3 wherein a portion of the alkyl orthosilicate used to form the silica or silica precursor is added to the slurry mixture while reducing the vanadium pentoxide to an oxidation state between about 3.5 and 4.6 and another portion is added to the coprecipitated mixture formed in accordance with step (b) before completion of the reacting of the phosphoric acid with the reduced vanadium.

5. A catalyst in accordance with claim 3 wherein at least a portion of the alkyl orthosilicate is added to the organic liquid medium so as to be present during reduction of the vanadium pentoxide in step (a) and thereby remove water formed by such reduction by reaction of the alkyl orthosilicate with the water so formed to convert the water to alcohol.

* * * * *